United States Patent [19]
Yamagata et al.

[11] Patent Number: 6,034,064
[45] Date of Patent: Mar. 7, 2000

[54] PEPTIDES AND THERAPEUTIC AGENT FOR AUTOIMMUNE DISEASES CONTAINING THE SAME

[75] Inventors: Nobuyuki Yamagata, Kawagoe; Kenji Ogata, Otawara; Masako Wagatsuma, Higashimurayama; Hitoshi Takanashi, Tokorozawa, all of Japan

[73] Assignee: Hoechst Pharmaceuticals & Chemicals K.K., Tokyo, Japan

[21] Appl. No.: 08/930,741

[22] PCT Filed: Apr. 3, 1996

[86] PCT No.: PCT/JP96/00917
§ 371 Date: Jan. 8, 1998
§ 102(e) Date: Jan. 8, 1998

[87] PCT Pub. No.: WO96/31529
PCT Pub. Date: Oct. 10, 1996

[30] Foreign Application Priority Data

Apr. 7, 1995 [JP] Japan ..................................... 7-117592

[51] Int. Cl.⁷ .............................. A61K 38/08; C07K 7/06
[52] U.S. Cl. .............................................. 514/15; 530/328
[58] Field of Search ................................ 514/15; 530/328

[56] References Cited

U.S. PATENT DOCUMENTS

| | | | |
|---|---|---|---|
| 3,926,938 | 12/1975 | Hughes et al. | 260/112.5 |
| 4,217,268 | 8/1980 | Hughes et al. | 260/112.5 |
| 4,622,386 | 11/1986 | Orlowski et al. | 530/307 |
| 4,639,510 | 1/1987 | Orlowski et al. | 530/307 |
| 4,659,804 | 4/1987 | Orlowski et al. | 530/307 |

FOREIGN PATENT DOCUMENTS

| | | |
|---|---|---|
| 0 298 474 A3 | 1/1989 | European Pat. Off. . |
| 0 347 105 A3 | 12/1989 | European Pat. Off. . |
| 2 184 729 | 7/1987 | United Kingdom . |
| WO 90/11294 | 10/1990 | WIPO . |
| WO 91/09623 | 7/1991 | WIPO . |
| WO 93/00365 | 1/1993 | WIPO . |
| WO 93/06135 | 4/1993 | WIPO . |
| WO 94/06823 | 3/1994 | WIPO . |
| WO 96/24370 | 8/1996 | WIPO . |

OTHER PUBLICATIONS

Yague et al., 'The Structure of V and J Segments in the Mouse', Nucleic Acids Research, vol. 16, No. 23, pp. 11355–11364, 1988.

Parker et al. 'Scheme for Ranking Potential HLA–A2 Binding Petides BSED on Independent Binding of Individual Peptide Side Chains', J. of immunology, 1994, vol. 152, No. 1. pp. 163–175.

Parker et al. 'Sequences Motifs Important for Peptides Binding to the Human MHC Class 1 Molecule, HLA–A2', J. Immunol., vol. 149, No. 11, pp. 3580–3587, 1992.

Sauma et al. 'Recognition by HLA–A2–Restricted Cytotoxic T Lymphocytes of Endogenously Generated and Exogenously Provided Synthetic Peptides Analogs of the Influenza a Virus Matrix Protein', Hum. Immunol. vol. 37, No. 4, pp. 252–258, 1993.

S. Sauma et al., "Recognition by HLA–A2–Restricted Cytotoxic T Lymphocytes of Endogenously Generated and Exogenously Provided Synthetic Peptide Analoques of the Influenza A Virus Matrix Protein", Hum. Immunol. 37 (4):252–258 (1993).

K. Parker et al., "Scheme for Ranking Potential HLA–A2 Binding Peptides Based on Independent Binding of Individual Peptide Side–Chains", J. Immunol., 152 (1) :163–175 (1994).

K. Parker et al., "Sequence Motifs Important for Peptide Binding to the Human MHC Class I Molecule, HLA–A2", J. Immunol., 149 (11) : 3580–3587 (1992).

S. Mohapatra et al., "Analysis of T–Cell Receptor αβ Chains of CD8+ Suppressor T Cells Induced by Tolergenic Conjugates of Antigen and Monomethoxypolyethylene Glycol", J. Immunol. 151 (3) :688–698 (1993).

T. Briner et al., "Peripheral T–Cell Tolerance Induced in Naive and Primed Mice by Subcutaneous Injection of Peptides from the Major Cat Allergen Fel d I", Proc. Natl. Acad. Sci. 90 (16) :7608–7612 (1993).

Database Toxlit on STN, No. 1972:33662 Toxlit; Barlet Jp, 'Effects of procine, salmon, and human calcitonin on urinary excretion of some electrolytes in sheep', J. Endocrinology (abstract), 1972.

Database Embase on STN, No. 74005418 Embase; Garijo et al. 'Effects of treatment with calcitonin in case of myeloma IgG with hypercalcemia and hyperuricemia', Rev. Clin. Esp. (abstract), 1973.

Database MARPAT on STN, No. 124:30425 Marpat; Katsumata et al., JP 07188297, Jul. 25, 1995.

*Primary Examiner*—Cecilia J. Tsang
*Assistant Examiner*—Anish Gupta
*Attorney, Agent, or Firm*—Finnegan, Henderson, Farabow, Garrett & Dunner, L.L.P.

[57] ABSTRACT

The present invention relates to a peptide having the following amino acid sequence:

Ala-Xaa1-Leu-Xaa2-Phe-Xaa3-Xaa4-Xaa5-(Xaa6)n (wherein Xaa1 and Xaa4 each independently represents an amino acid residue which may have an alkyl or heteroalkyl side chain which may be substituted by a hydroxy, amino or guanidyl group;

Xaa2 and Xaa6 each independently represents an amino acid residue which may have an alkyl or heteroalkyl side chain which may be substituted by a hydroxyl group;

Xaa3 and Xaa5 each independently represents an amino acid residue which may have a hydrophobic side chain; and n stands for 1 or 0), or derivatives thereof; and a modification thereof.

The peptide or derivatives thereof according to the present invention is useful as a pharmaceutical composition for the prevention and treatment of autoimmune diseases, rejection reaction attendant on the organ transplantation, inflammation or the like.

10 Claims, 9 Drawing Sheets

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
           (A) LENGTH: 9 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO:1:

Ala Lys Leu Thr Phe Gly Lys Gly Thr
      1               5

(2) INFORMATION FOR SEQ ID NO:2:

(i) SEQUENCE CHARACTERISTICS:
           (A) LENGTH: 8 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO:2:

Ala Lys Leu Thr Phe Gly Lys Gly
      1               5

(2) INFORMATION FOR SEQ ID NO:3:

(i) SEQUENCE CHARACTERISTICS:
           (A) LENGTH: 8 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO:3:

Ala Ala Leu Thr Phe Gly Lys Gly
      1               5

(2) INFORMATION FOR SEQ ID NO:4:

(i) SEQUENCE CHARACTERISTICS:
           (A) LENGTH: 8 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO:4:

Ala Lys Leu Ala Phe Gly Lys Gly
      1               5

(2) INFORMATION FOR SEQ ID NO:5:

(i) SEQUENCE CHARACTERISTICS:
           (A) LENGTH: 8 amino acids
           (B) TYPE: amino acid
           (C) STRANDEDNESS: single
           (D) TOPOLOGY: linear

```
        (ii) MOLECULE TYPE: peptide (xi) SEQUENCE DESCRIPTION: SEQ ID NO:5:

Ala Lys Leu Thr Phe Ala Lys Gly
    1               5

(2) INFORMATION FOR SEQ ID NO:6:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:6:

Ala Lys Leu Thr Phe Gly Ala Gly
    1               5

(2) INFORMATION FOR SEQ ID NO:7:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:7:

Ala Lys Leu Thr Phe Gly Lys Ala
    1               5

(2) INFORMATION FOR SEQ ID NO:8:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:8:

Ala Lys Ala Thr Phe Gly Lys Gly
    1               5

(2) INFORMATION FOR SEQ ID NO:9:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:9:

Ala Lys Leu Thr Ala Gly Lys Gly
    1               5

(2) INFORMATION FOR SEQ ID NO:10:

(i) SEQUENCE CHARACTERISTICS:
            (A) LENGTH: 7 amino acids
            (B) TYPE: amino acid
            (C) STRANDEDNESS: single
```

```
        (D) TOPOLOGY: linear (ii) MOLECULE TYPE: peptide (xi) SEQUENCE DESCRIPTION: SEQ ID NO:10:

Lys Leu Thr Phe Gly Lys Gly
   1               5
```

PEPTIDES AND THERAPEUTIC AGENT FOR AUTOIMMUNE DISEASES CONTAINING THE SAME

TECHNICAL FIELD OF THE INVENTION

The present invention relates to peptides or derivatives thereof. The peptides or derivatives thereof according to the present invention are useful for the antigen non-specific suppressive treatment of abnormally augmented immunoreaction in autoimmune diseases. Having an anti-inflammatory effect, it is also useful for the treatment of the inflammation.

Accordingly, the present invention relates to the fields concerned with peptides or derivatives thereof and also with pharmaceuticals containing the same.

1. Background of the Invention

Autoimmune diseases are induced by the continuous production of an antibody or lymphocyte which reacts with a component of the own tissue. In the autoimmune diseases, described specifically, the break-down of immunologic tolerance heightens immune response to own organic components, which causes the reaction between an autoantibody or autoreactive T cell so produced and an autoantigen or cell corresponding thereto, thereby causing cellular dysfunction or tissue damages. At present, 50 or more types of autoimmune diseases are known and according to the spreading degree of a lesion over the organs, they can be classified into organ specific autoimmune diseases and organ nonspecific autoimmune diseases.

Examples of the former diseases include insulin-dependent diabetes mellitus in which a lesion is caused by the selective destruction of B cells in pancreatic island of Langerhans, Basedow disease and Hashimoto disease in which thyroid dysfunction is caused by the antibody against a thyroid stimulating hormone receptor, myasthenia gravis which has muscle contraction lowered by an antibody against an acetylcholine receptor of the striated muscle, and autoimmune hemolytic anemia in which hemolysis is caused by the antibody against the erythrocyte.

Examples of the latter diseases include chronic rheumatoid arthritis in which generalized disorders in the osseous or cartilaginous tissue are considered to occur, triggered by the aggregation of IgG and anti-IgG antibodies (rheumatoid factors), systemic lupus erythematosus in which a disturbing reaction is caused by the deposition of antibodies against DNA or nuclear components to the kidney, joint or skin, Sj Ügren syndrome in which dysfunction occurs owing to the lymphocytic infiltration into the salivary gland or lacrimal gland and systemic organolesion such as interstitial nephritis occurs concurrently at certain frequency, and multiple sclerosis in which disseminated demyelination nidi and gliosis appear in the substantia alba of the central nervous system and they cause systemic motor paralysis, ophthalmopathy, paresthesia or the like.

2. Prior Art

For the treatment of autoimmune diseases, it is the common practice to administer an immunosuppressant typified by a gluco-steroid preparation, cyclosporin A or FK 506. The treatment using such a preparation is, however, accompanied by the drawback such as serious side effects, for example, infectious diseases, nephrotoxicity of the drug itself or carcinogenesis, which result from wide spectrum of immunosuppression [Sadao Kashiwazaki, ΠSogo Rinsho Ⅱ, 43 (9), 1725–1729 (1994)].

In recent years, there have been some attempts to treat autoimmune diseases without using such an immunosuppressant with wide spectrum.

Upon reaction with an antigen, B cells recognize the antigen itself, while T cells recognize the complex of an MHC molecule on the surface of the antigen presenting cell and an antigen peptide fitted in the groove of the MHC molecule. The MHC molecule differs with individuals and human T cells having MHC congenial to a certain antigen shows good response to this antigen. This is one of the reasons why some human beings are likely to be reactive to a certain antigen. On the other hand, T-cell antigen receptors (T cell receptors: TcR) can be classified into several families. There is a substance which activates T cells, binding with one or some of the TcR families and the substance is called a superantigen. The superantigen activates a larger number of T cells compared with those in the case of the ordinary immunoreaction so that it happens to cause a large reaction, leading to a disease. For the activation of T cells, binding of a partner molecule (ligand) to the adhesion molecule on the surface is necessary in addition to the recognition of the antigen. The reaction of T cells can, therefore, be inhibited by blockading the adhesion molecule, or the reaction can be amplified by the enhanced expression of the ligand of the partner cell.

It is reported that among T cell groups, there exist T cells which suppress the immunoreaction which are so-called suppressor T cells [Tada and Takemori, J. Exp. Med., 140, 239 (1974)]. It is elucidated that these T cells produce soluble immunosuppressive factors for suppressing antigen specific antibody production [Tada, et al., J. Immul., 111, 952 (1973)]. The relationship between the soluble immunosuppressive factors and a TcR alfa chain is reported [Dorf, et al., J. Immunol., 145, 2809–2819 (1990)]. Experimental allergic encephalomyelitis (EAE) which is a model of multiple sclerosis is induced by the administration of basic myelin protein. In the EAE, presence of a T cell antigen receptor (disease specific TcR) which is expressed specifically on the pathogenic lymphocyte is known. The treatment method by using an antibody against a disease-specific TcR or TcR peptide vaccine has, therefore, been developed [Howell, et al., Science, 251, 430–432 (1991); Vandenbrk, et al., Nature, 341, 541∓544(1989)]. Such a treatment method of autoimmune diseases is considered to be associated with less serious side effects compared with the method employing an immunosuppressant such as gluco-steroid preparation or cyclosporin A. The above method can only be applied to the case where the T cell or antigen which has caused a disease is circumscribed within a markedly narrow range. It is considered to be difficult to apply the above method to autoimmune diseases, such as chronic rheumatoid arthritis, of which antigen is not yet determined and in which a plural number of pathogenic lymphocytes exist. This method requires the establishment of individual suppressor T cell specific to each antigen and analysis of its TcR. Under the present state where the suppressor T cells derived from human being cannot be established easily, it is extremely difficult to develop the above TcR as an immunosuppressive agent.

On the other hand, reported is a case where immunologic tolerance is induced by using a peptide having an antigen-derived amino acid sequence [Greenstein, et al., Proc. Natl. Acad. Sci. USA, 9, 7608–7612 (1993)]. As a method of using an immunosuppressant composed of a TcR peptide fragment, disclosed is a method in which TcR beta-chain derived polypeptide (composed of 13 amino acid residues at the minimum) is used for the treatment of autoimmune diseases, particularly, chronic rheumatoid arthritis (Japanese Language Laid-Open Publication No. HEI 6-511241); and a method in which a TcR peptide fragment of pathogenic T cells which cause multiple sclerosis is administered to suppress the onset of EAE (WO90/11294). Mohapatra et al. have proved that a synthetic peptide composed of 15 amino acid residues containing CDR3 (complementarity determining region), which is a specific antigen determining site of TcR derived from suppressor T-cell, has an immunosuppressive effect [J. Immunol., 151, 688–698 (1993)].

The above-described peptide fragments are no better than an immunosuppressive agent characterized by having antigen specificity so that a problem that it cannot be used for the treatment of all the autoimmune diseases has remained unsolved.

SUMMARY OF THE INVENTION

An object of the present invention is to overcome the above described disadvantages or defects of the conventional methods, thereby providing a therapeutic agent for autoimmune diseases, which has antigen nonspecific immunosuppressive effects and can therefore be used for the treatment of autoimmune diseases of which antigens are not yet been determined.

Another object of the present invention is to provide a therapeutic agent for autoimmune diseases, which can be used for the treatment of autoimmune diseases accompanied with inflammation.

A further object of the present invention is to provide a peptide which is characterized by having a low molecular weight compared with that employed in the conventional method so that it can be prepared at a low cost and has markedly reduced side effects such as occurrence of antigenecity due to frequent administration.

As a result of an extensive investigation on the mutual relationship between the amino acid sequence of a protein or peptide fragment originated from a protein such as CDR3 of TcR derived from suppressor T cells and a therapeutic agent for autoimmune diseases, the present inventors have found that there exist some peptides having suppressive activity against antigen nonspecific IgG production. Finding that a peptide composed of 9 amino acid residues, which is shown as Sequence ID No. 1 in the Sequence Listing, suppresses not only the anti-ovalbumin (OVA) antibody production but also anti-keyhole-lympet-hemocyanin (KLH) antibody production in each in vivo experiment, the present inventors have completed the present invention. Incidentally, OVA and KLH are typical antigens used as immunogens (Immunology Dictionary, 1993, Tokyo Kagaku Dojin, pp101 and 130).

In general, TcR derived from suppressor T cells corresponds with one by one specifically to various antigens. The peptide of the present invention, on the other hand, suppresses antibody production against different antigens such as OVA and KLH and, therefore, has antigen nonspecific immunosuppressive activity.

The present inventors have also found that the peptide composed of 9 amino acid residues, which is shown as Sequence ID No. 1 in the Sequence Listing, suppresses the onset of experimental allergic encephalomyelitis (EAE), a model of multiple sclerosis, which is one of autoimmune diseases for which T cells are responsible. In addition, it is surprising that they have found the peptide composed of 9 amino acid residues, which is indicated by Sequence ID No. 1 in the Sequence Listing, suppresses the edema in a carrageenin-induced paw edema model and, therefore, has an anti-inflammatory effect. The peptide of the present invention has a property of immunosuppression by suppressing T cell activities as well as anti-inflammation.

As a result of extensive efforts to develop a low-molecular weight peptide which has less antigenicity and can be easily synthesized, the present inventors have found that the peptide composed of 8 amino acid residues, which is shown as Sequence ID No. 2 in the Sequence Listing, suppresses not only the anti-OVA antibody production but also anti-KLH production, in each in vivo experiment. The present inventors have also found by the alanine substitution method [Geysen H. M., et al., J. Immunol. Methods, 102, 259–274 (1987)] that there exist, in some peptides having a certain consensus amino acid sequence, peptides having an antigen nonspecific IgG production suppressive activity. Finding that such peptides having a general amino acid sequence suppresses not only the anti-ovalbumin (OVA) antibody production but also anti-keyhole-lympet-hemocyanin (KLH) antibody production in each in vivo experiment, the present inventors have completed the present invention.

Accordingly, the present invention relates to a peptide having an amino acid sequence represented by the following formula:

Ala-Xaa1-Leu-Xaa2-Phe-Xaa3-Xaa4-Xaa5-(Xaa6)n (wherein Xaa1 and Xaa4 each independently represents an amino acid residue which may have an alkyl or heteroalkyl side chain which may be substituted by a hydroxy, amino or guanidyl group;

Xaa2 and Xaa6 each independently represents an amino acid residue which may have an alkyl or heteroalkyl side chain which may be substituted by a hydroxyl group;

Xaa3 and Xaa5 each independently represents an amino acid residue which may have a hydrophobic side chain; and n stands for 1 or 0), or derivatives thereof; a pharmaceutical composition containing the same; and a method for the treatment of diseases using thereby.

BRIEF DESCRIPTION OF THE DRAWINGS

FIG. 1 is a chart of the chromatogram of Peptide (I). Peptide (I) obtained according to the present invention had a purity of 100%.

FIG. 2 is a chart of the chromatogram of Peptide (II). Peptide (II) obtained according to the present invention had a purity of 99.6%.

FIG. 3 is a chart of the chromatogram of Peptide (III). Peptide (III) obtained according to the present invention had a purity of 98.8%.

FIG. 4 is a chart of the chromatogram of Peptide (IV). Peptide (IV) obtained according to the present invention had a purity of 97.2%.

FIG. 5 is a chart of the chromatogram of Peptide (V). Peptide (V) obtained according to the present invention had a purity of 98.5%.

FIG. 6 is a chart of the chromatogram of Peptide (VI). Peptide (VI) obtained according to the present invention had a purity of 98.4%.

FIG. 7 is a chart of a chromatogram of Peptide (VII). Peptide (VII) obtained according to the present invention had a purity of 97.9%.

FIG. 8 is a chart of the chromatogram of Peptide (VIII). Peptide (VIII) obtained according to the present invention had a purity of 98.1%.

FIG. 9 is a chart of the chromatogram of Peptide (IX). Peptide (IX) obtained according to the present invention had a purity of 97.5%.

FIG. 10 is a chart of the chromatogram of Peptide (X). Peptide (X) obtained according to the present invention had a purity of 98.2%.

DISCLOSURE OF THE INVENTION

Figure 1:
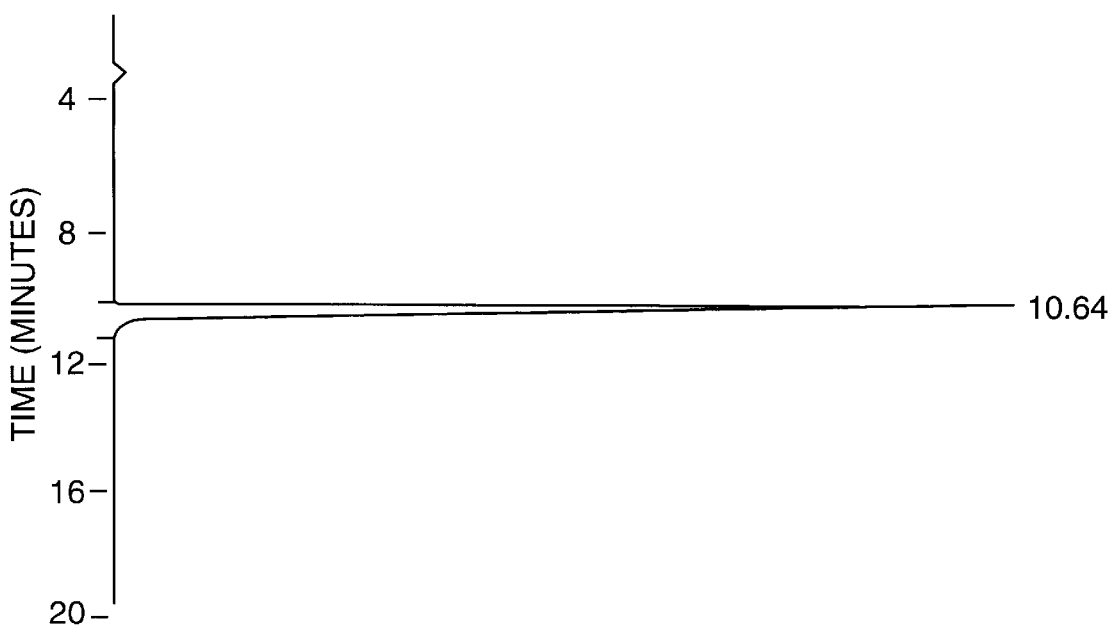

The present invention relates to a peptide having an amino acid sequence represented by the following formula:
Ala-Xaa1-Leu-Xaa2-Phe-Xaa3-Xaa4-Xaa5-(Xaa6)n (wherein Xaa1 and Xaa4 each independently represents an amino acid residue which may have an alkyl or heteroalkyl side chain which may be substituted by a hydroxy, amino or guanidyl group;

Xaa2 and Xaa6 each independently represents an amino acid residue which may have an alkyl or heteroalkyl side chain which may be substituted by a hydroxyl group;

Xaa3 and Xaa5 each independently represents an amino acid residue which may have a hydrophobic side chain; and n stands for 1 or 0, with the proviso that the case where Xaa2 represents glycine is excluded), or a derivative thereof.

Xaa1 and Xaa4 each independently represents an amino acid residue which may have an alkyl or heteroalkyl side chain which may be substituted by a hydroxy, amino or guanidyl group. Examples may include Lys, Arg, His and Ala.

Xaa2 and Xaa6 each independently represents an amino acid residue which may have an alkyl or heteroalkyl side chain which may be substituted by a hydroxyl group. Examples may include Thr and Ala.

Xaa3 and Xaa5 each independently represents an amino acid residue which may have a hydrophobic side chain. Examples may include Gly and Ala.

The term "alkyl" as used herein means a group which embraces primary, secondary and tertiary saturated C1–15, preferably C1–10 alkyl groups which may be linear or branched. The term "heteroalkyl" as used herein means a group in which at least one of the carbon atoms of the above-described C1–15, preferably C1–10 "alkyl" group has been substituted with a like number of hetero atoms such as sulfur (S) or oxygen (O) [ordinarily, in the form of a (thio)ester or (thio)ether]. n stands for 1 or 0.

In the peptide derivative of the present invention, all or part of the amino acids may be in the D form, a functional group having an active hydrogen may be substituted with an appropriate protective group or the carboxyl group at the C-terminal may be in the form of a carboxy derivative such as amide or ester. No particular limitation is imposed on the protective group suitable for the substitution with the amino or carboxyl group in the peptide, however, an acetyl group (Ac) or t-butoxycarbonyl group (tBoc) is preferred. As a carboxy derivative at the C terminal, an amide is preferred.

The conversion into a peptide derivative can bring about an improvement in the stability.

Described specifically, the present invention pertains to a peptide having the following amino acid sequence;
Ala-Xaa1-Leu-Xaa2-Phe-Xaa3-Xaa4-Xaa5-(Xaa6)n (wherein Xaa1 and Xaa4 each independently represents any one of Lys, Art, His and Ala;

Xaa2 and Xaa6 each independently represents Thr or Ala;

Xaa3 and Xaa5 each independently represents Gly or Ala; and n stands for 1 or 0), or derivative thereof.

More specifically, the present invention relates to a peptide having an amino acid sequence selected from the group consisting of the following amino acid sequences:

Ala-Lys-Leu-Thr-Phe-Gly-Lys-Gly-Thr (Seq. ID No. 1),
Ala-Lys-Leu-Thr-Phe-Gly-Lys-Gly (Seq. ID No. 2),
Ala-Ala-Leu-Thr-Phe-Gly-Lys-Gly (Seq. ID No. 3),
Ala-Lys-Leu-Ala-Phe-Gly-Lys-Gly (Seq. ID No. 4),
Ala-Lys-Leu-Thr-Phe-Ala-Lys-Gly (Seq. ID No. 5),
Ala-Lys-Leu-Thr-Phe-Gly-Ala-Gly (Seq. ID No. 6), and
Ala-Lys-Leu-Thr-Phe-Gly-Lys-Ala (Seq. ID No. 7).

Still more specifically, the present invention relates to a peptide or derivative thereof selected from the group consisting of the peptides and derivatives thereof represented by the following formulas (I) to (XII):

| | |
|---|---|
| Ala-Lys-Leu-Thr-Phe-Gly-Lys-Gly-Thr (Seq. ID No. 1) | (I) |
| DAla-DLys-DLeu-DThr-DPhe-Gly-DLys-Gly-DThr | (II) |
| Ac-Ala-Lys-Leu-Thr-Phe-Gly-Lys-Gly-Thr | (III) |
| tBoc-Ala-Lys-Leu-Thr-Phe-Gly-Lys-Gly-Thr | (IV) |
| Ac-DAla-DLys-DLeu-DThr-DPhe-Gly-DLys-Gly-DThr | (V) |
| Ac-DAla-DLys-DLeu-DThr-DPhe-Gly-DLys-Gly-DThr-NH2 | (VI) |
| Ala-Lys-Leu-Thr-Phe-Gly-Lys-Gly (Seq. ID No. 2) | (VII) |
| Ala-Ala-Leu-Thr-Phe-Gly-Lys-Gly (Seq. ID No. 3) | (VIII) |
| Ala-Lys-Leu-Ala-Phe-Gly-Lys-Gly (Seq. ID No. 4) | (IX) |
| Ala-Lys-Leu-Thr-Phe-Ala-Lys-Gly (Seq. ID No. 5) | (X) |
| Ala-Lys-Leu-Thr-Phe-Gly-Ala-Gly (Seq. ID No. 6) | (XI) |
| Ala-Lys-Leu-Thr-Phe-Gly-Lys-Ala (Seq. ID No. 7) | (XII) |

(wherein D represents a D-form, Ac represents an acetyl group and tBoc represents a t-butoxycarbonyl group), or a derivative thereof.

No particular limitation is imposed on the preparation process of the peptide having an amino acid sequence represented by the following formula:
Ala-Xaa1-Leu-Xaa2-Phe-Xaa3-Xaa4-Xaa5-(Xaa6)n (wherein Xaa1 and Xaa4 each independently represents an amino acid residue which may have an alkyl or heteroalkyl side chain which may be substituted by a hydroxy, amino or guanidyl group;

Xaa2 and Xaa6 each independently represents an amino acid residue which may have an alkyl or heteroalkyl side chain which may be substituted by a hydroxyl group;

Xaa3 and Xaa5 each independently represents an amino acid residue which may have a hydrophobic side chain; and n stands for 1 or 0), or a derivative thereof. For example, it is possible to synthesize a peptide by using a peptide synthesizer in accordance with the solid-phase peptide synthesis (Fmoc) in accordance with an ordinary manner, followed by purification by a reverse-phase HPLC column. Peptides (II) to (XII) can also be synthesized by the peptide synthesizer and they can be chemically converted as needed.

The peptide of the present invention is preferred to have soluble physicochemical properties. Because the peptide of the present invention has a low molecular weight, side effects such as antigenicity occurrence can be significantly reduced even after frequent administration and besides, its toxicity is very low. The present invention also pertains to a pharmaceutical composition containing a peptide having an amino acid sequence represented by the following formula:

Ala-Xaa1-Leu-Xaa2-Phe-Xaa3-Xaa4-Xaa5-(Xaa6)n (wherein Xaa1 and Xaa4 each independently represents an amino acid residue which may have an alkyl or heteroalkyl side chain which may be substituted by a hydroxy, amino or guanidyl group;

Xaa2 and Xaa6 each independently represents an amino acid residue which may have an alkyl or heteroalkyl side chain which may be substituted by a hydroxyl group;

Xaa3 and Xaa5 each independently represents an amino acid residue which may have a hydrophobic side chain; and n stands for 1 or 0), or a derivative thereof; or a pharmaceutical composition containing said peptide or derivative thereof and a pharmaceutically acceptable carrier.

Described specifically, the present invention pertains to a peptide having an amino acid sequence represented by the following formula:

Ala-Xaa 1-Leu-Xaa2-Phe-Xaa3-Xaa4-Xaa5-(Xaa6)n (wherein Xaa1 and Xaa4 each independently represents any one of Lys, Arg, His and Ala;

Xaa2 and Xaa6 each independently represents Thr or Ala;

Xaa3 and Xaa5 each independently represents Gly or Ala; and n stands for 1 or 0), or derivative thereof.

More specifically, the present invention pertains to a pharmaceutical composition containing a peptide having an amino acid sequence selected from the group consisting of the following amino acid sequences:

Ala-Lys-Leu-Thr-Phe-Gly-Lys-Gly-Thr (Seq. ID No. 1),
Ala-Lys-Leu-Thr-Phe-Gly-Lys-Gly (Seq. ID No. 2),
Ala-Ala-Leu-Thr-Phe-Gly-Lys-Gly (Seq. ID No. 3),
Ala-Lys-Leu-Ala-Phe-Gly-Lys-Gly (Seq. ID No. 4),
Ala-Lys-Leu-Thr-Phe-Ala-Lys-Gly (Seq. ID No. 5),
Ala-Lys-Leu-Thr-Phe-Gly-Ala-Gly (Seq. ID No. 6) and
Ala-Lys-Leu-Thr-Phe-Gly-Lys-Ala (Seq. ID No. 7), or derivatives thereof; or a pharmaceutical composition containing said peptide or derivatives thereof and a pharmaceutically acceptable carrier.

Still more specifically, the present invention also pertains to a pharmaceutical composition containing a peptide or derivatives thereof selected from the group consisting of peptides and derivatives thereof represented by the following formulas (I) to (XII):

| | |
|---|---|
| Ala-Lys-Leu-Thr-Phe-Gly-Lys-Gly-Thr (Seq. ID No. 1) | (I) |
| DAla-DLys-DLeu-DThr-DPhe-Gly-DLys-Gly-DThr | (II) |
| Ac-Ala-Lys-Leu-Thr-Phe-Gly-Lys-Gly-Thr | (III) |
| tBoc-Ala-Lys-Leu-Thr-Phe-Gly-Lys-Gly-Thr | (IV) |
| Ac-DAla-DLys-DLeu-DThr-DPhe-Gly-DLys-Gly-DThr | (V) |
| Ac-DAla-DLys-DLeu-DThr-DPhe-Gly-DLys-Gly-DThr-NH2 | (VI) |
| Ala-Lys-Leu-Thr-Phe-Gly-Lys-Gly (Seq. ID No. 2) | (VII) |
| Ala-Ala-Leu-Thr-Phe-Gly-Lys-Gly (Seq. ID No. 3) | (VIII) |
| Ala-Lys-Leu-Ala-Phe-Gly-Lys-Gly (Seq. ID No. 4) | (IX) |
| Ala-Lys-Leu-Thr-Phe-Ala-Lys-Gly (Seq. ID No. 5) | (X) |
| Ala-Lys-Leu-Thr-Phe-Gly-Ala-Gly (Seq. ID No. 6) | (XI) |
| Ala-Lys-Leu-Thr-Phe-Gly-Lys-Ala (Seq. ID No. 7) | (XII) |

(wherein D represents a D-form, Ac represents an acetyl group and tBoc represents a t-butoxycarbonyl group);

or a pharmaceutical composition containing said peptide or derivatives thereof and a pharmaceutically acceptable carrier.

In the peptide derivatives used for the pharmaceutical composition of the present invention, all or part of the amino acids may be in the D form, a functional group having an active hydrogen may be substituted with an appropriate protective group or the carboxyl group at the C-terminal may be in the form of a carboxy derivative such as amide or ester. No particular limitation is imposed on the protective group suitable for the substitution with the amino or carboxyl group in the peptide, however, an acetyl group (Ac) or t-butoxycarbonyl group (tBoc) is preferred. As a carboxy derivative at the C terminal, an amide is preferred. The conversion into a peptide derivative can bring about an improvement in the stability.

The above-described pharmaceutical composition of the present invention is useful particularly for the treatment of autoimmune diseases. Accordingly, the present invention provides a pharmaceutical composition for the treatment of autoimmune diseases.

The pharmaceutical composition of the present invention for the treatment of autoimmune diseases is characterized by its antigen nonspecificity. The peptide or derivatives thereof according to the present invention suppress the activity of T-cells so that the present invention also relates to a pharmaceutical composition for the treatment of one or more than one diseases selected from the group consisting of multiple sclerosis, chronic rheumatoid arthritis, systemic lupus erythematosus, SjÜgren syndrome, Basedow disease, Hashimoto disease and autoimmune hemolytic anemia.

The above-described pharmaceutical composition of the present invention is also useful for the prevention and treatment of rejection episode attendant to the organ transplantation. Accordingly, the present invention provides a pharmaceutical composition for the prevention and treatment of rejection episode attendant to the organ transplantation.

Moreover, the above-described pharmaceutical composition of the present invention has an anti-inflammatory effect and is useful as an anti-inflammatory agent. Accordingly, the present invention provides a pharmaceutical composition for the treatment of inflammation.

The present invention also relates to a method of treatment for autoimmune diseases, which comprises administering a pharmaceutically effective amount of the above-described peptide or derivatives thereof. The present invention also relates to a method of treatment for one or more than one diseases selected from the group consisting of multiple sclerosis, chronic rheumatoid arthritis, systemic lupus erythematosus, SjÜgren syndrome, Basedow disease, Hashimoto disease and autoimmune hemolytic anemia, which comprises administering a pharmaceutically effective amount of the above-described peptide or derivatives thereof. The present invention also pertains to a preventive and curative method of rejection episode attendant to the organ transplantation, which comprises administering a pharmaceutically effective amount of the above-described peptide or derivatives thereof.

The present invention also pertains to a method of treatment for inflammation, which comprises administering a pharmaceutically effective amount of the above-described peptide or derivatives thereof.

The present invention also relates to the use of the above-described peptide or derivatives thereof for the preparation of a pharmaceutical composition for the treatment of autoimmune diseases. The present invention also relates to the use of the above-described peptide or derivative thereof for the preparation of a pharmaceutical composition for the treatment of one or more than one diseases selected from the group consisting of multiple sclerosis, chronic rheumatoid arthritis, systemic lupus erythematosus, SjÜgren syndrome, Basedow disease, Hashimoto disease and autoimmune hemolytic anemia.

The present invention also relates to the use of the above-described peptide or derivatives thereof for the preparation of a pharmaceutical composition for the prevention and treatment of rejection episode attendant to the organ transplantation. The present invention also relates to the use of the above-described peptide or derivatives thereof for the preparation of a pharmaceutical composition for the treatment of inflammation.

Although the clinical dosage of the peptide of the present invention varies depending on the administration method, age, weight or conditions of each patient, or the like, it typically falls within a range of 0.05 to 500 mg, preferably 0.1 to 100 mg per day and adult.

As an administration method, intravenous administration can be employed. In addition to the ordinary intravenous injection, transfusion is also possible.

As an injection preparation, the peptide of the present invention or the derivatives thereof can be formulated, for example, into a powdery preparation for injection. In this case, the injection preparation can be obtained by adding one or more than one suitable water-soluble excipients selected from mannitol, sucrose, lactose, maltose, glucose, fructose, or the like added to the powdery preparation, dissolving the resulting mixture in water, pouring portions of the resulting solution in vials or ampoules, lyophilizing and then hermetically sealing. It is also possible to administer in systemic the powdery preparation through the nose or lungs as a fine-particulate aerosol preparation. In addition, the powdery preparation can be administered orally after added with a suitable excipient or the like.

In the present invention, the suppressive effects of anti-OVA antibody production and anti-KLH antibody production in mice were studied by the ELISA method. Compared with the non-administered group, the peptide of the present invention exhibited significantly high suppressive activity against anti-OVA antibody production. Even in comparison with a peptide fragment composed of 15 amino acid residues originated from CDR3, the peptide of the present invention showed markedly high antibody production suppressive activity. Compared with the non-administered group, the peptide of the present invention exhibited markedly high suppressive activity against anti-KLH antibody production.

In addition, the suppressive effects against the onset of experimental allergic encephalomyelitis (EAE) in mice was examined. Compared with the non-administered group, the peptide of the present invention showed significant suppressive effect against the onset of EAE. Moreover, the suppressive effect of the peptide of the present invention on the rat carrageenin-induced paw edema model was examined, resulting in considerably high edema suppressive effect compared with the non-administered group.

It has not so far been reported that a low molecular weight peptide which is derived from a TcR alfa chain J region and can be artificially synthesized has an antigen nonspecific immunosuppressive effect. The peptide or derivatives of the present invention are useful as a therapeutic agent of autoimmune diseases, particularly, a pharmaceutical composition for the treatment of one or more than one diseases selected from the group consisting of multiple sclerosis, chronic rheumatoid arthritis, systemic lupus erythematosus, Sjügren syndrome, Basedow disease, Hashimoto disease and autoimmune hemolytic anemia. It has also an anti-inflammatory effect so that it is useful as a therapeutic agent for, among autoimmune diseases, those accompanied with inflammation such as chronic rheumatoid arthritis. Moreover, the peptide of the present invention has antibody production suppressive effects so that it is useful as a preventive or therapeutic agent for immediate type allergy in which IgE is concerned, such as pollinosis, atopic dermatitis, asthma, anaphylactic shock or hay fever, or drug allergy.

The present invention will hereinafter be described in detail by examples but it should however be borne in mind the present invention is not limited to or by the following examples.

Example 1

Synthesis of Peptides

Synthesis of Peptide (I)

Peptide (I) was synthesized by the solid-phase method (Fmoc) by using a peptide synthesizer ("Model 430 A", Applied Biosystems Inc.).

An amino acid having an N-terminal protected with a 9-fluorenylmethyloxycarbonyl (Fmoc) group was coupled on a p-hydroxymethylphenoxymethylpolystyrene (HMP) resin by the method which is described below.

First, the amino acid on the resin were deprotected at room temperature for 30 minutes by using 20% piperidine/N-methylpyrrolidone (NMP), followed by washing twice with NMP and then with 50% dichloromethane (DCM)/methanol. After washing, a peptide diluted with a 50% o-benzotriazol-1-yl-N,N,NF,NF-tetramethyluronium-hexafluoro-phosphate (HBTU)/DCM was added and a coupling reaction was conducted at room temperature for around 60 to 120 minutes. The above-described steps were repeated for coupling of all the amino acids. After the completion of the reaction, the N-terminal Fmoc group was removed using 50% HBTU/DCM, followed by recovery of the free peptide from the resin by using 95% trifluoroacetic acid (TFA). The peptide so recovered was diluted with a 5% acetic acid solution, followed by the purification by the reverse-phase HPLC.

Synthesis of Peptides (II), (III), (IV), (V) and (VI)

Peptides (II), (III), (IV), (V) and (VI) were synthesized by the solid-phase method (tBoc) by using a peptide synthesizer ("Beckman 990c").

An amino acid having an N-terminal protected with a t-butyloxycarbonyl (tBoc) group was coupled on a resin by the method which is described below. Incidentally, a phenylacetamidomethyl (Pam) resin was used for the synthesis of a peptide having a carboxyl group as a C-terminal and a 4-methylbenzhydrylamine (MBHA) resin was used for the synthesis of a peptide having an amide group as a C-terminal.

First, the amino acid on the resin was deprotected at room temperature for 25 minutes by using 50% TFA/DCM, followed by washing twice with isopropanol, DIPEA and DCM, respectively. Then, a peptide diluted with 50% DMF/DCM was added and coupling reaction was carried out at room temperature for around 60 to 120 minutes. The above-described steps were repeated and coupling reactions of all the amino acids were completed. Peptide (IV) was obtained by recovering the free peptide from the resin by the HF method (J. M. Stewart et al., Pierce Chemical Co., Rockford, Ill., 1984), diluting the resulting free peptide with a 5% acetic acid solution and then purifying the reverse-phase HPLC method. Peptide (II) was obtained by removing the tBoc group at the N-terminal by using 50% TFA/DCM, recovering the free peptide from the resin by the HF method, diluting with a 5% acetic acid solution, and then purifying by the reverse-phase HPLC method. Peptides (III), (V) and (V) were each obtained by adding an acetyl group (Ac) to the N-terminal by using 20% acetic anhydride, recovering the free peptide by the HF method, diluting with a 5% acetic acid solution and then purifying by the reverse-phase HPLC method.

Detection of the peptide purity thus synthesized

The purity of each peptide thus synthesized was determined using a C-18 column (Vydac Corp.) by the reverse-phase HPLC method. With a linear gradient from 5% to 25% of acetonitrile/purified water as a mobile phase, the elution peak was detected by measuring an absorbance at 215 nm.

FIG. 1 is a chart of the chromatogram of Peptide (I). Peptide (I) synthesized above had a purity of 100%.

Figure 2:
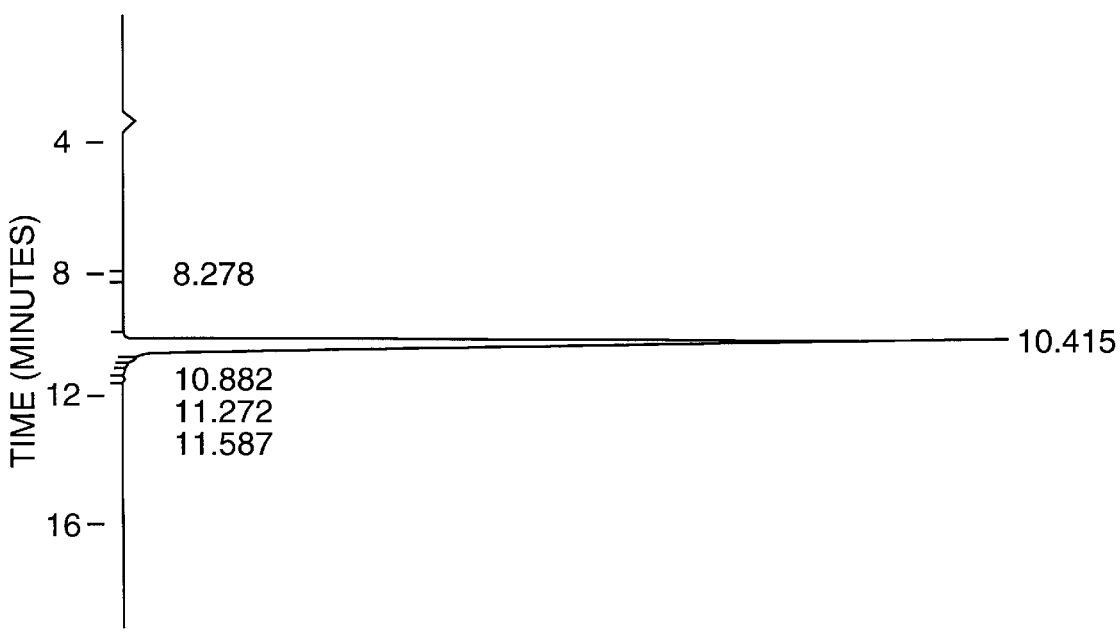

FIG. 2 is a chart of the chromatogram of Peptide (II). Peptide (II) synthesized above had a purity of 99.6%.

Figure 3:
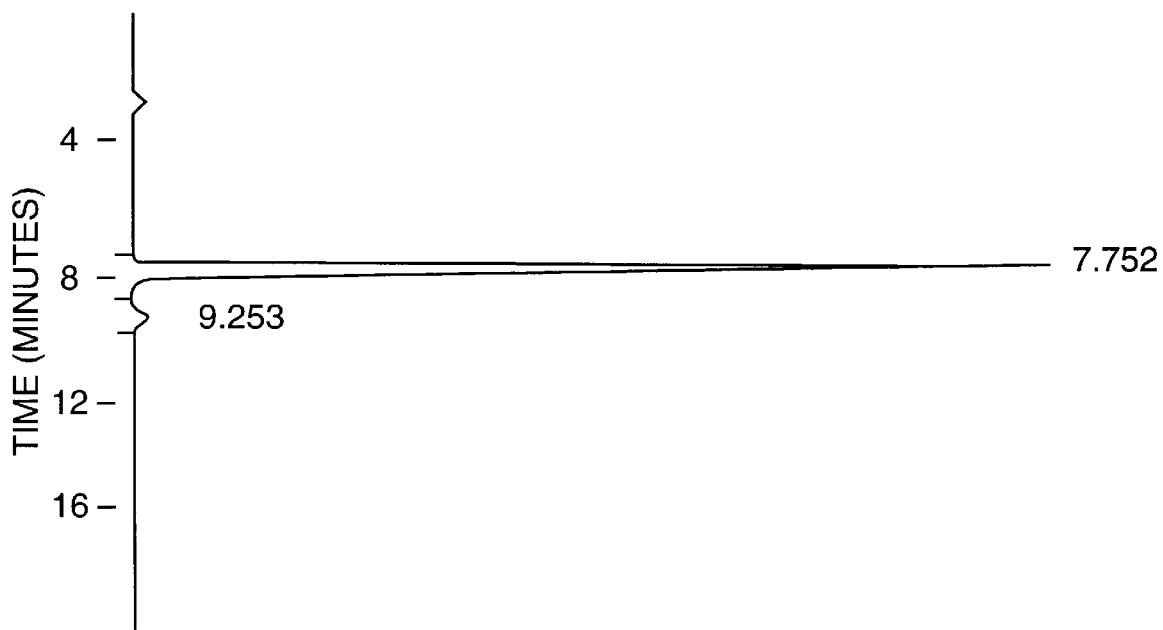

FIG. 3 is a chart of the chromatogram of Peptide (III). Peptide (III) synthesized had a purity of 98.8%.

Figure 4:
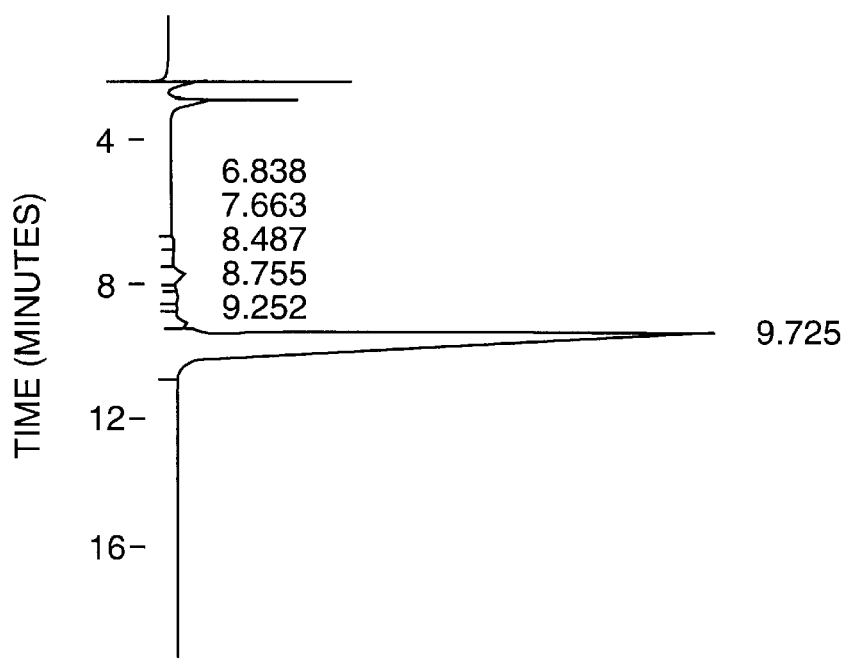

FIG. 4 is a chart of the chromatogram of Peptide (IV). Peptide (IV) synthesized above had a purity of 97.2%.

Figure 5:

FIG. 5 is a chart of the chromatogram of Peptide (V). Peptide (V) synthesized above had a purity of 98.5%.

Figure 6:

FIG. 6 is a chart of the chromatogram of Peptide (VI). Peptide (VI) synthesized had a purity of 98.4%.

Example 2

Measurement of the Suppressive Effect of Peptide (I) on Anti-OVA Antibody Production in Mice.

Day 5 and day 3 prior to the antigen administration, Peptide (I) composed of 9 amino acid residues as indicated by Sequence ID No. 1 in the Sequence Listing of the present invention and a synthetic peptide 15 composed of 15 amino acid residues derived from clone 17.2 TcR, which peptide had been reported by Mohapatra et al. as described above, 100 g each, were dissolved in 200 of physiological saline and each solution thus obtained was subcutaneously administered to 9-week-old Balb/c mice. As a control, a non-administered group to which the same amount of physiological saline was administered was employed. In 200 l of physiological saline, 100 g of OVA (Sigma Chemical Co.) were dissolved, followed by subcutaneous administration. Blood was collected on day 21 after antigen administration and an antibody titer was measured by the method described below.

OVA was diluted to 10 g/ml with phosphate buffered saline (PBS) and 50 l portions of the solution were poured in a 96-well microplate. The coating operation was conducted overnight at 40° C. The microplate was then washed three times with a 0.05% Tween®-20-containing PBS (T-PBS). 200 l portions of 0.5% casein-containing tris buffered physiological saline (casein TBS) were poured in each well and the microplate was allowed to stand at room temperature for one hour. The microplate was then washed three times with T-PBS. After the serum of the blood collected from the mice was diluted to 1/200 with 0.5% casein TBS, 50 l portions of the diluted serum were poured in each well and the plate was allowed to stand for one hour (primary reaction).

After the completion of the primary reaction, the microplate was washed three times with T-PBS. Fifty l portions of anti-mouse IgG-peroxidase-labeled antibody (TAGO Co.) diluted to 1/4000 with 0.5% casein TBS were poured in each well, followed by reaction at room temperature for one hour (secondary reaction). After the completion of the secondary reaction, the plate was washed three times again. Fifty l portions of a substrate liquid/chromogen (chromogen substrate: Behringwerke AG) were poured in each well, followed by reaction at room temperature for 30 minutes. After the completion of the reaction, 0.5N diluted sulfuric acid was added to terminate the reaction and an absorbance at 450 nm was measured by a calorimeter ("BEP-II", product of Behringwerke AG/Germany) with an absorbance at 650 nm as a control. The results are shown in Table 1.

TABLE 1

Suppressive effect of Peptide (I) of this invention on anti-OVA antibody production in mouse

| Treated with | Anti OVA Ig-G antibody titer (unit) |
| --- | --- |
| Non-administered group | 59 ± 40.0 |
| Peptide 15 derived from clone 17.2 | 13.5 ± 12.0 |
| Peptide (I) | 8.8 ± 10.8 |

From the above results, it has been found that compared with the non-administered group, antibody production was significantly suppressed in the mice to which synthetic peptide 15 derived from clone 17.2 and Peptide (I) of this invention were administered, respectively. Incidentally, each group consisted of 8 mice.

Example 3

Measurement of the Suppressive Effect of Peptides (I) to (VI) on Anti-KLH Antibody Production in Mice Day 5 and day 3 prior to the antigen administration, 100 μg of each Peptide (I) to (VI) of the present invention composed of 9 amino acid residues indicated by Sequence ID No. 1 in the Sequence Listing were dissolved in 200 μl of physiological saline. The resulting solution was subcutaneously administered to 9-week-old Balb/c mice. As a control, a non-administered group to which the same amount of physiological saline was administered was employed. In 200 μl of physiological saline, 25 μg of KLH were dissolved as an antigen and the resulting solution was subcutaneously administered. The blood was collected on day 21 after antigen administration and an antibody titer was measured by the method which is described below.

KLH was diluted to 10 μg/ml with a phosphate buffered physiological saline (PBS). Fifty μl portions of the resulting solution were poured into a 96-well microplate and the plate was allowed to stand at 4iC overnight. After the microplate was washed three times with 0.05% Tween®-20-containing PBS (T-PBS), 200 µl portions of 0.5% casein tris-buffered physiological saline (casein TBS) were poured into wells, respectively. The microplate was then allowed to stand at room temperature for one hour. The microplate was washed three times with T-PBS and 50 µl portions of the mouse serum diluted to 1/200 with casein TBS were poured into the wells, followed by reaction for one hour (primary reaction).

The resulting microplate was washed three times with T-PBS, to which 50 µl portions of an anti-mouse IgG-peroxidase-labeled antibody (TAGO Co.) diluted to 1/4000 with casein TBS were poured. The reaction was effected at room temperature for one hour (secondary reaction). After the completion of the secondary reaction, the plate was washed three times again. Fifty µl portions of a substrate liquid/chromogen (chromogen substrate: Behringwerke AG) were poured into wells, respectively, followed by reaction at room temperature for 30 minutes. After the completion of the reaction, 0.5N diluted sulfuric acid was added to terminate the reaction and an absorbance at 450 nm was measured by a calorimeter ("BEP-II ", product of Behringwerke AG/Germany) with the absorbance at 650 nm as a control. The results are shown in Table 2.

TABLE 2

Suppressive effect of Peptides of this invention on anti-KLH antibody production

| Treated with | Anti-KLH IgG antibody titer (unit ± SD) |
| --- | --- |
| Peptide (I) | 78.7 ± 28.3 |
| Peptide (II) | 48.4 ± 13.1 |
| Peptide (III) | 50.1 ± 25.8 |
| Peptide (IV) | 48.5 ± 24.9 |
| Peptide (V) | 37.7 ± 17.7 |
| Peptide (VI) | 29.5 ± 19.5 |
| Physiological saline | 133.8 ± 48.2 |

From the above results, it has been found that compared with the non-administered group to which physiological saline had been administered, antibody production was significantly suppressed in the mice groups to which Peptides (I) to (VI) had been administered, respectively. Incidentally, each group consisted of 8 mice.

It has been understood from the results of Examples 2 and 3, the peptides of the present invention had antigen non-specific immunosuppressive action.

Example 4

Onset Suppressive Effect of Peptide (I) on EAE Model Mice

As an antigen, guinea pig spinal chord homogenate was employed. The guinea pig spinal chord homogenate was diluted with PBS to be 6.6 mg/ml, followed by the addition of the equivalent amount of FreundFs complete adjuvant. The resulting mixture was formed into an emulsion by an ultrasonic sonicator. The resulting emulsion was administered to two areas under the lateral skin in a total amount of 300 µl. Day 5 and day 3 prior to antigen administration, and 5 days a week for 4 weeks after antigen administration, the solution of Peptide (I) dissolved in 100 µl physiological saline was subcutaneously administered to a 14-week old SJL mouse. Incidentally, in order to increase an onset ratio, 400 µg/100 µl of pertussis toxin (PTX) were intravenously administered as an enhancer on the day of antigen administration and two days after antigen administration. Observation of the onset was performed from day 14 to day 28 after primary antigen administration. The onset was scored based on the following standard criteria [Pettinelli, C. B., Fritz, D. E., and McFarlin, D. E. J. Immunl., 129, No. 3, 1024–1028 (1982)]. In Table 3, values of average score+ standard deviation (SD) in each administration group on day 22, day 25 and day 28 after primary antigen administration are shown. Incidentally, each group consisted of 8 mice and SteelFs two tail method was used for statistical analysis.

Score 0: No abnormality
Score 1: Slight paralysis of hind leg with tail weakness
Score 2: Moderate paralysis of hind leg with tail weakness
Score 3: Total paralysis of hind leg
Score 4: Slight paralysis of forward leg with total paralysis of hind leg
Score 5: Total paralysis of all leg
Score 6: Death from paralysis The results are shown in Table 3.

TABLE 3

Onset suppressive effect of Peptide (I) of this invention on EAE model mice (average score ± SD)

| | Day 22 | Day 25 | Day 28 |
| --- | --- | --- | --- |
| 25 µg/body | 0.3 ± 0.4 | 0.1 ± 0.3 | 0.0 ± 0.0 |
| 5 µg/body | 0.4 ± 0.7 | 1.0 ± 1.1 | 0.7 ± 0.8 |
| 1 µg/body | 1.6 ± 1.8 | 0.9 ± 1.1 | 1.8 ± 1.9 |
| physiological saline | 3.6 ± 2.5 | 4.2 ± 2.6 | 4.2 ± 2.6 |

It has been recognized that the onset of EAE was suppressed by the administration of synthetic Peptide (I) of the present invention. Particularly, in 5 µg/body administered group, the onset was suppressed on day 25 and day 28 with a significant difference of 5% compared with the physiological saline administered group. In the 25 µg/body administered group, the onset was suppressed from day 22 with a significant difference of 5% compared with the physiological saline administration group. Moreover, from day 25, the onset was suppressed with a significant difference of 1%.

It has been found from Example 4 that the peptide of the present invention is effective for the treatment of multiple sclerosis.

Example 5

Suppressive Effect of Peptide (I) on Rat Carrageenin-Induced Paw Edema Model

To physiological saline, λ-carrageenin ("PICNIN-A", Zushi Chemical Co.) was added at the final concentration of 1 w/v %, and it was heated in a boiling water bath to dissolve I-carrageenin completely. The resulting solution was then allowed to stand at room temperature. Before the experiment, the solution was dissolved completely by heating in a boiling water bath and was allowed to stand in a water bath of about 60iC until administration. Immediately after 50 µl of Peptide (I) of the present invention or physiological saline (non-administered group) were administered subcutaneously to the left leg of Splague-Dawley rats (6 weeks old, male), 50 µl of the 1% carrageenin solution were administered to the same site. The paw volume was measured using plethysmometer (product of BM Instrument Co.) every one hour for 5 hours after carrageenin administration. Incidentally, each group consisted of 10 rats and DunnetFs two tail method was used for statistical analysis.

The results are shown in Table 4.

TABLE 4

| Suppressive effect of Peptide (I) of this invention on edema (%) | | | |
|---|---|---|---|
| | 1 hour | 2 hours | 5 hours |
| 0.2 μg/site | 2.3 | 3.9 | 4.8 |
| 10 μg/site | 30.2 | 37.3 | 27.5 |

It has been recognized that the onset of edema one hour after the administration of carrageenin tended to be suppressed by the administration of Peptide (I) of the present invention. In the 10 μg/site administered group, the onset of edema was suppressed two hours on and after the administration of carrageenin with a significant difference of 5% and the tendency to suppress the edema onset was observed five hours after the administration of carrageenin. From the above, it has been found that the peptide of the present invention has anti-inflammatory action. Moreover, the present inventors conducted the following experiment in order to find effective low-molecular weight peptides.

Example 6
Synthesis of Peptides

Peptides (VII), (VIII), (IX), (X), (XI), (XII), (XIII), (XIV) and (XV) were synthesized and purified in a similar manner to Example 1 by using a peptide synthesizer ("Model 430A", ABI Co.).

Ala-Lys-Leu-Thr-Phe-Gly-Lys-Gly (Seq. ID No. 2) (VII)
Ala-Ala-Leu-Thr-Phe-Gly-Lys-Gly (Seq. ID No. 3) (VIII)
Ala-Lys-Leu-Ala-Phe-Gly-Lys-Gly (Seq. ID No. 4) (IX)
Ala-Lys-Leu-Thr-Phe-Ala-Lys-Gly (Seq. ID No. 5) (X)
Ala-Lys-Leu-Thr-Phe-Gly-Ala-Gly (Seq. ID No. 6) (XI)
Ala-Lys-Leu-Thr-Phe-Gly-Lys-Ala (Seq. ID No. 7) (XII)
Ala-Lys-Ala-Thr-Phe-Gly-Lys-Gly (Seq. ID No. 8) (XIII)
Ala-Lys-Leu-Thr-Ala-Gly-Lys-Gly (Seq. ID No. 9) (XIV)
Lys-Leu-Thr-Phe-Gly-Lys-Gly (Seq. ID No. 10) (XV)

Detection of the purity of peptides so synthesized was performed.

The purity of each peptide so synthesized was detected in a similar manner to Example 1.

Figure 7:
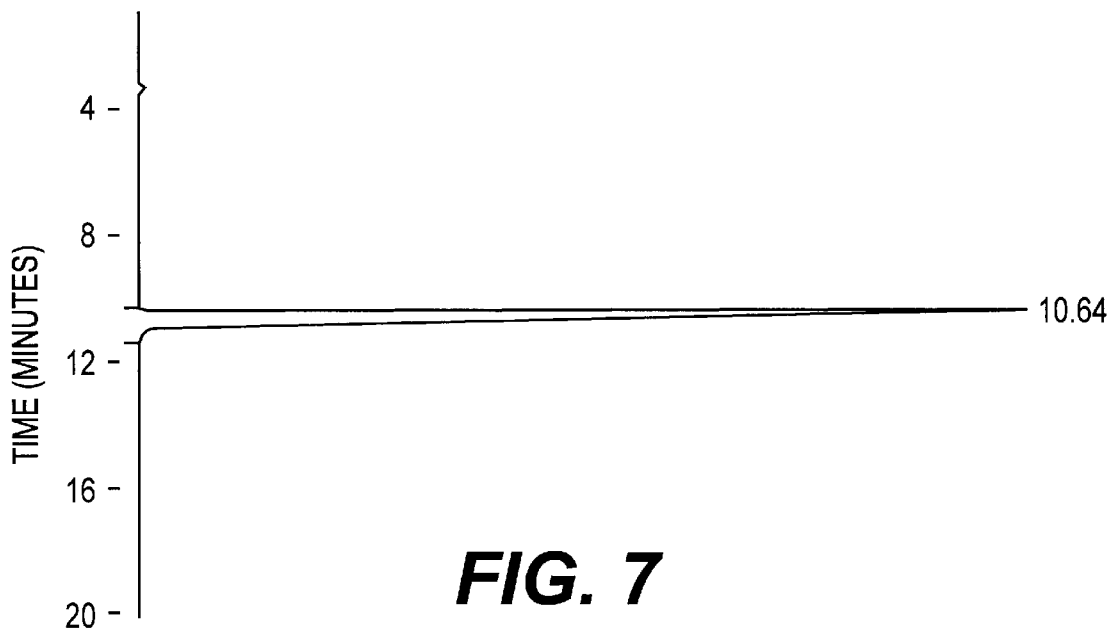

FIG. 7 is a chart of the chromatogram of Peptide (VII). Peptide (VII) so synthesized had a purity of 97.9%.

Figure 8:
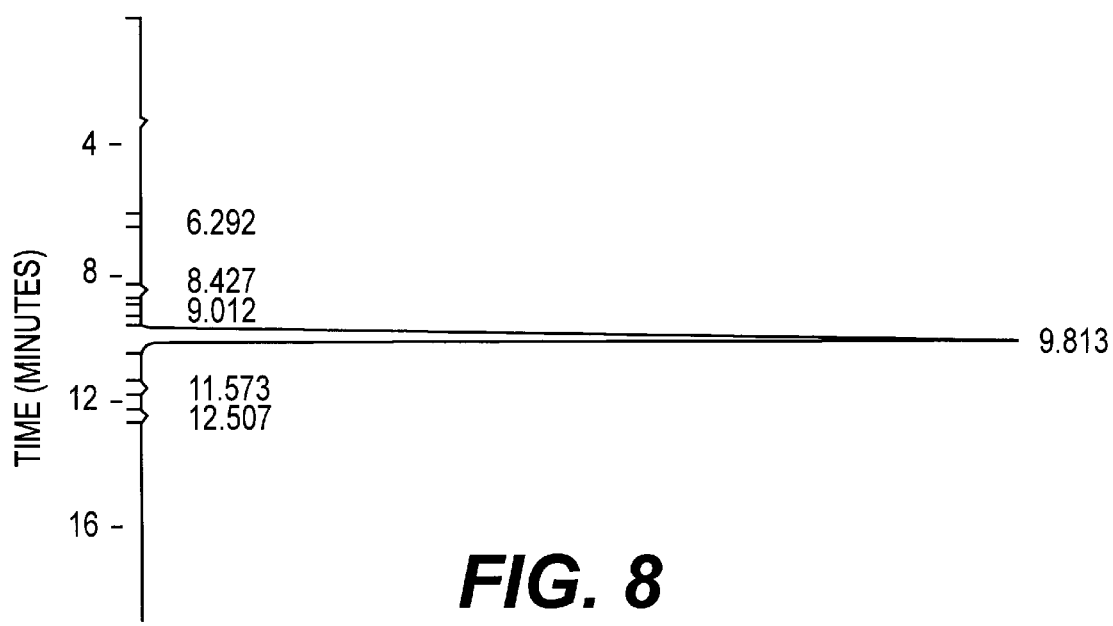

FIG. 8 is a chart of the chromatogram of Peptide (VIII). Peptide (VIII) so synthesized had a purity of 98.1%.

Figure 9:
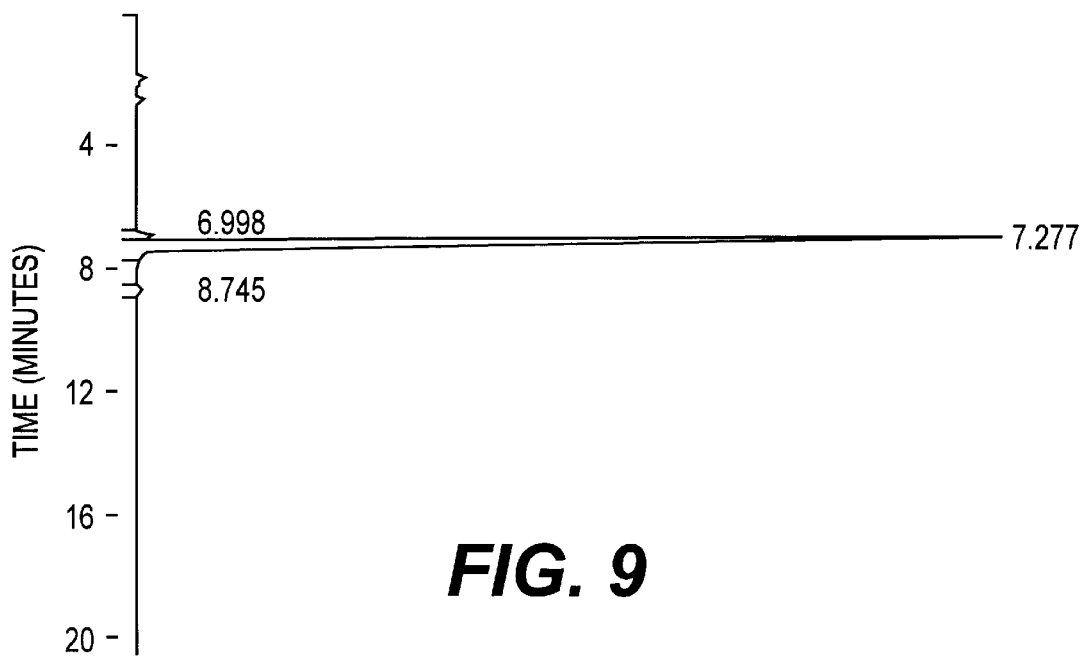

FIG. 9 is a chart of the chromatogram of Peptide (IX). Peptide (IX) so synthesized had a purity of 97.5%.

Figure 10:
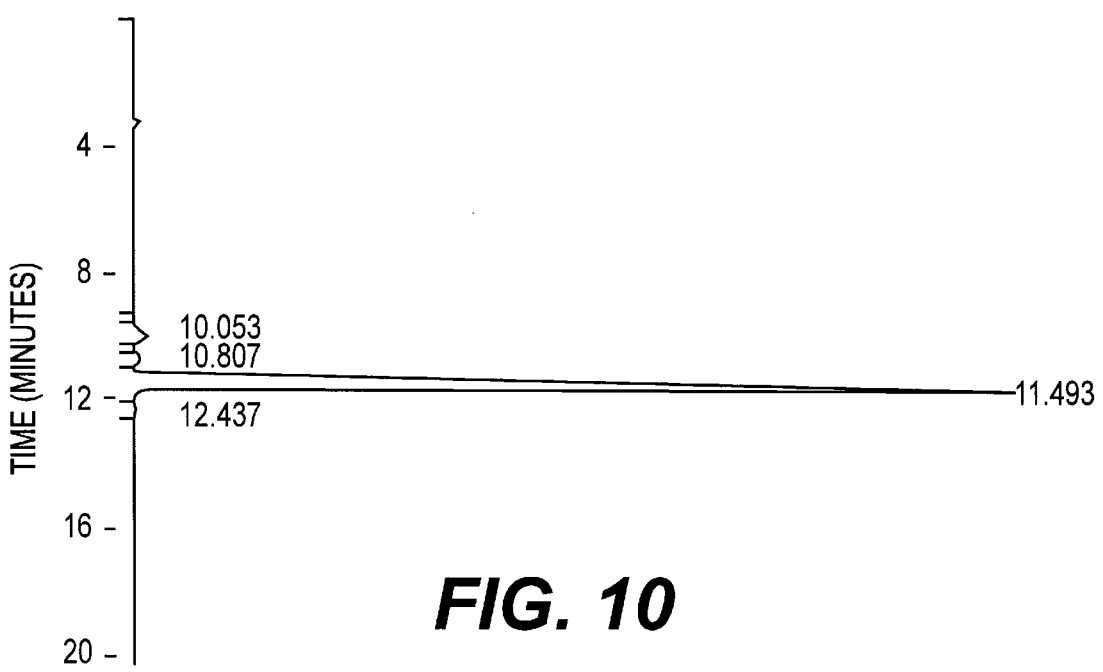

FIG. 10 is a chart of the chromatogram of Peptide (X). Peptide (X) so synthesized had a purity of 98.2%.

Figure 11:
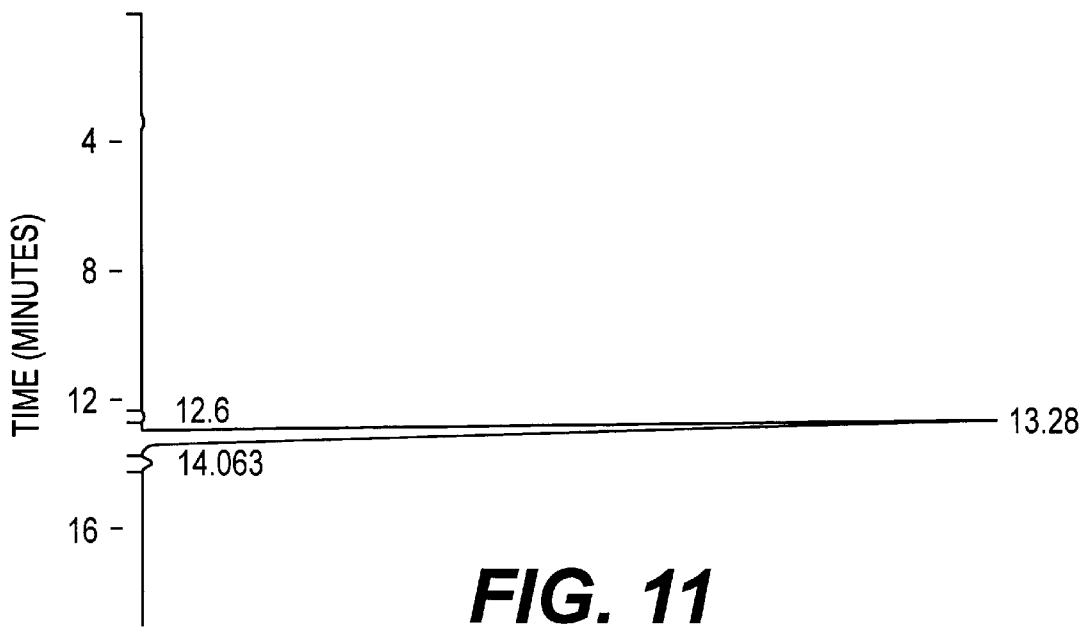
FIG. 11 is a chart of the chromatogram of Peptide (XI). Peptide (XI) obtained according to the present invention had a purity of 97.6%.

FIG. 11 is a chart of the chromatogram of Peptide (XI). Peptide (XI) so synthesized had a purity of 97.6%.

Figure 12:
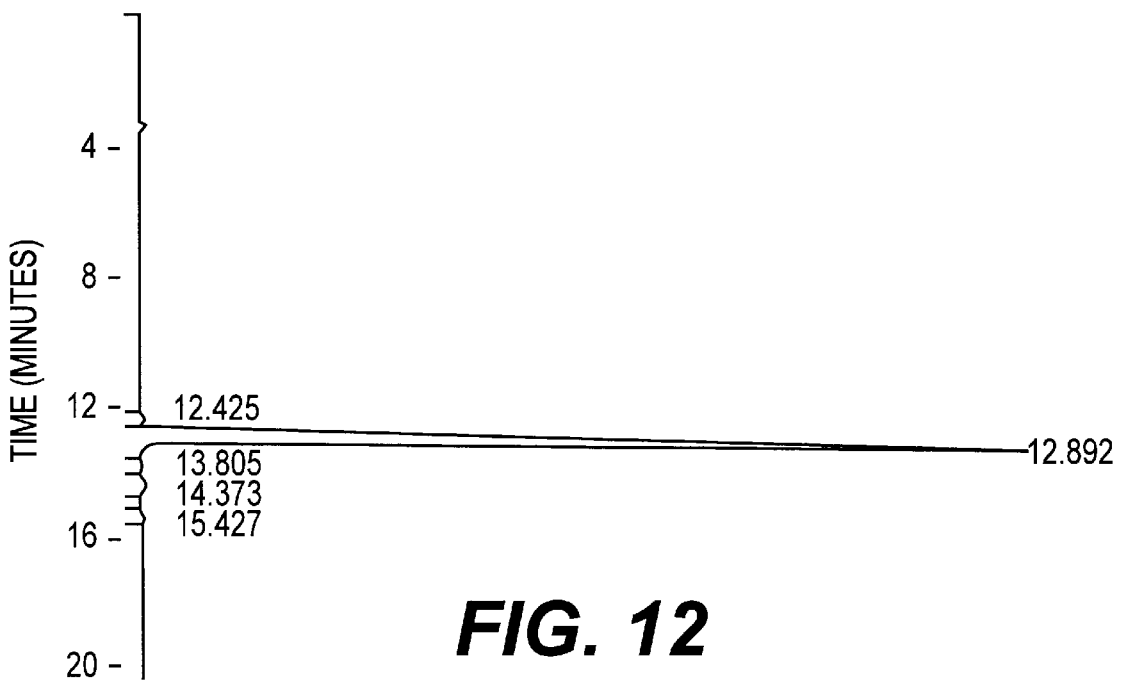
FIG. 12 is a chart of the chromatogram of Peptide (XII). Peptide (XII) obtained according to the present invention had a purity of 97.5%.

FIG. 12 is a chart of the chromatogram of Peptide (XII). Peptide (XII) so synthesized had a purity of 97.5%.

Figure 13:
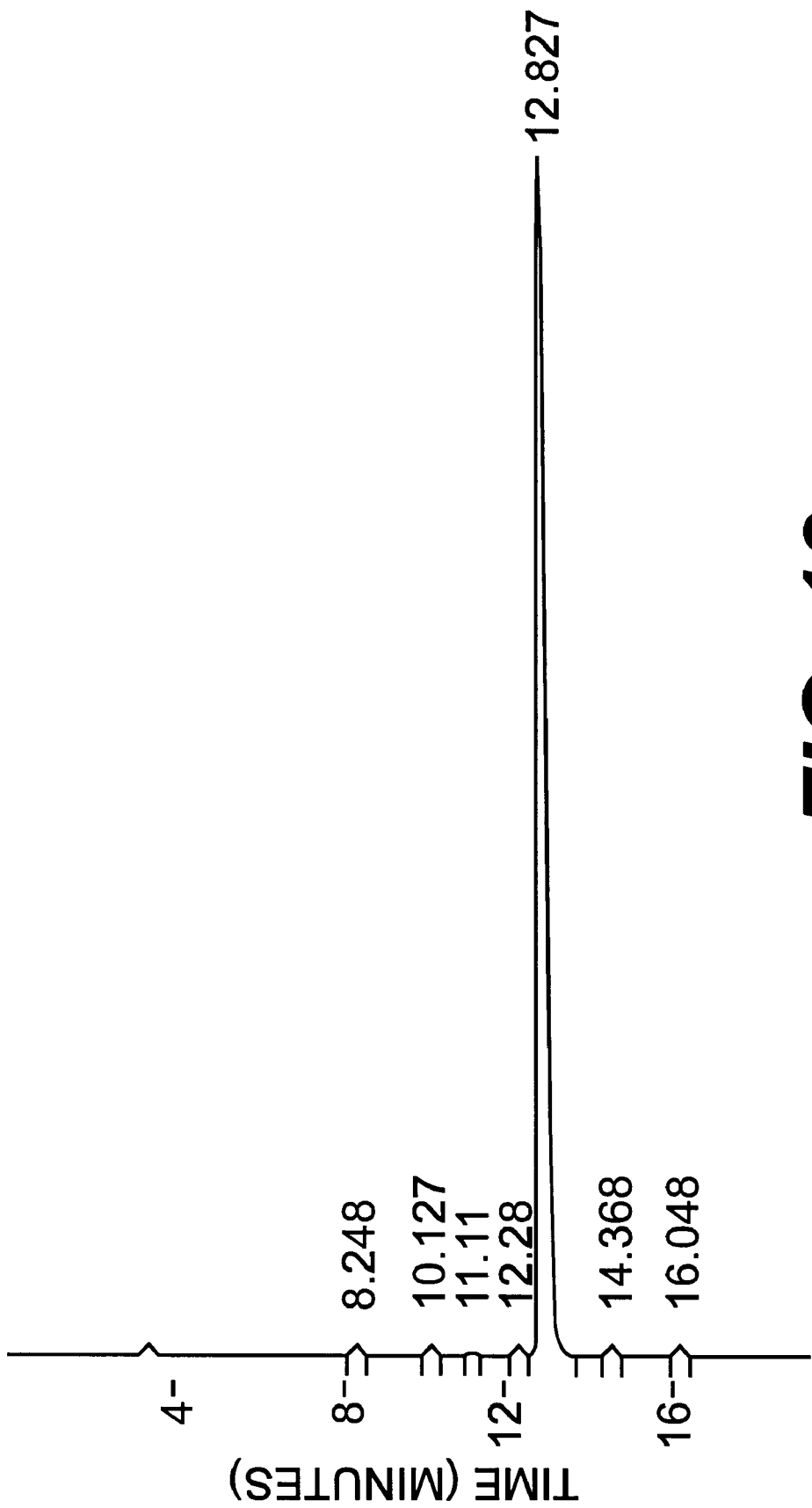
FIG. 13 is a chart of the chromatogram of Peptide (XIII). Peptide (XIII) obtained according to the present invention had a purity of 98.2%.

FIG. 13 is a chart of the chromatogram of Peptide (XIII). Peptide (XIII) so synthesized had a purity of 98.2%.

Figure 14:
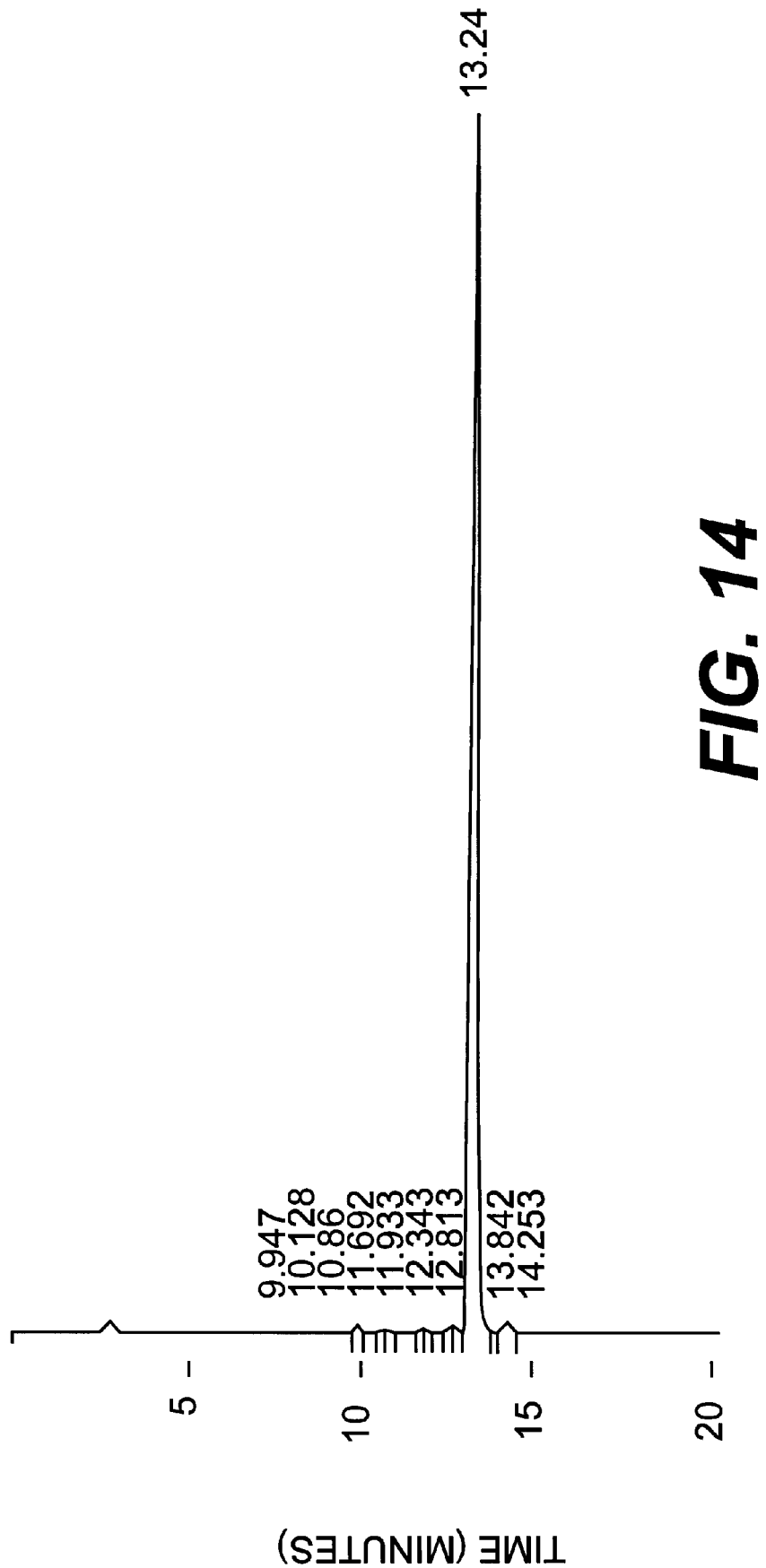
FIG. 14 is a chart of the chromatogram of Peptide (XIV). Peptide (XIV) obtained according to the present invention had a purity of 98.6%.

FIG. 14 is a chart of the chromatogram of Peptide (XIV). Peptide (XIV) so synthesized had a purity of 98.6%.

Figure 15:
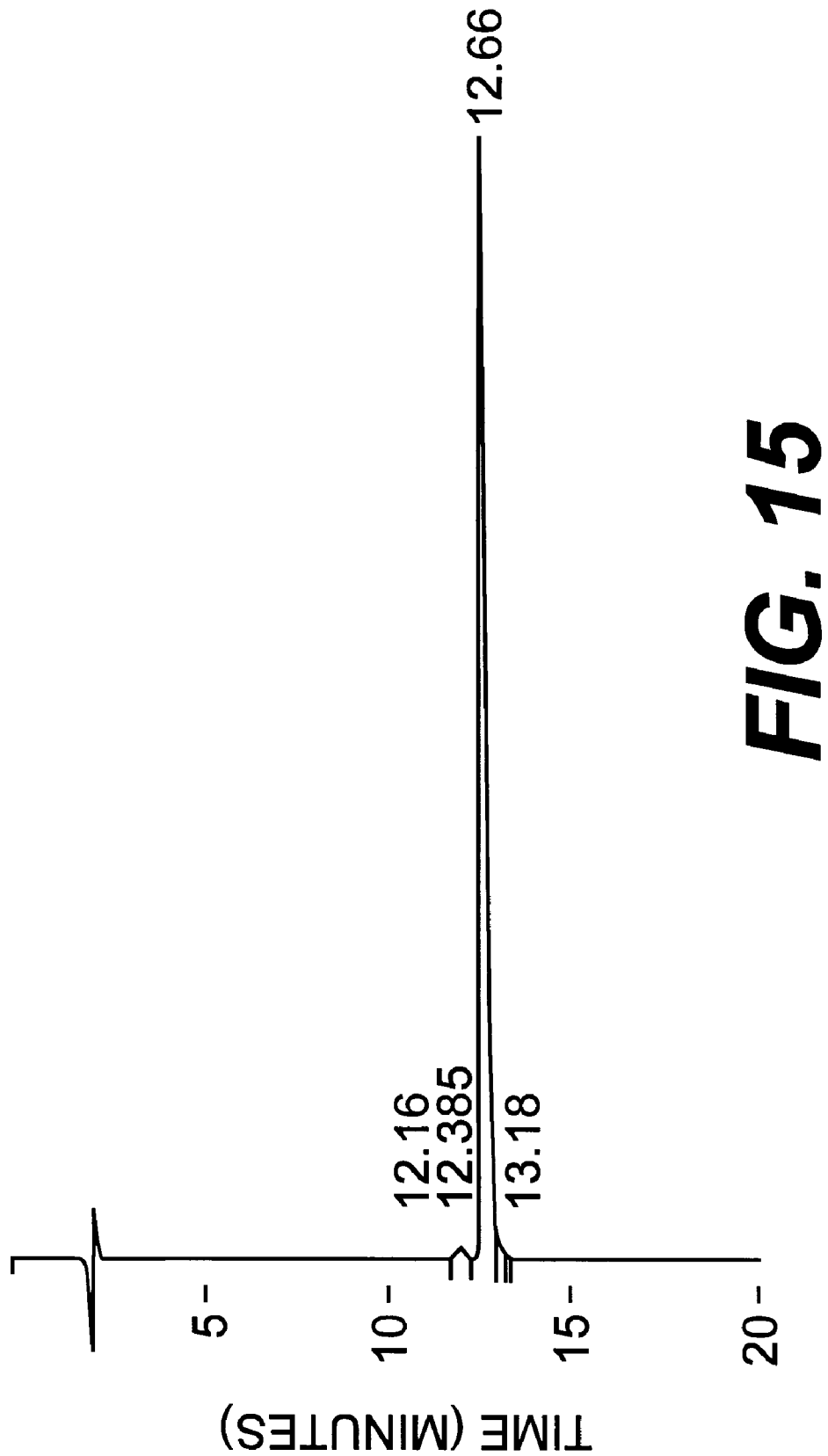
FIG. 15 is a chart of the chromatogram of Peptide (XV). Peptide (XV) obtained according to the present invention had a purity of 100%.

FIG. 15 is a chart of the chromatogram of Peptide (XV). Peptide (XV) so synthesized had a purity of 100%.

Example 7
Measurement of the Suppressive Effect of Peptides (I), (VII) to (XV) on the Anti-KLH Antibody Production in Mice In a similar manner to Example 3, suppressive effects of Peptides (I), (VII) to (XV) on anti-KLH antibody production in mice were studied. The results are shown in Table 5.

TABLE 5

| Treated with | Anti-KLH antibody titer (unit ± SD) |
|---|---|
| Peptide (I) | 39.5 ± 16.1 |
| Peptide (VII) | 25.9 ± 15.4 |
| Peptide (VIII) | 44.9 ± 18.1 |
| Peptide (IX) | 33.9 ± 13.7 |
| Peptide (X) | 26.5 ± 22.0 |
| Peptide (XI) | 19.9 ± 15.9 |
| Peptide (XII) | 49.5 ± 40.1 |
| Peptide (XIII) | 68.9 ± 25.1 |
| Peptide (XIV) | 59.9 ± 32.8 |
| Peptide (XV) | 86.4 ± 27.8 |
| Physiological saline (non-administered group) | 115.7 ± 61.3 |

Compared with the non-administered group and Peptide (I) administered group, the antibody production was significantly suppressed in the mice to which Peptide (VII), (IX), (X) or (XI) was administered. The antibody production was, on the other hand, not suppressed in the mice to which Peptide (VIII), (XII), (XIII), (XIV) or (XV) was administered, compared with Peptide (I) administered group. Incidentally, each group consisted of 8 mice.

From the above results, it has been found that the minimum peptide permitting the suppression of the antibody production is composed of 8 amino acid residues as indicated by the Sequence ID No. 2 of the Sequence Listing.

Example 8 Suppressive effect of Peptides (I), (VII) to (XIV) on the anti-OVA antibody production in mice; and identification of the minimum unit of peptide and essential amino acid exhibiting these effects.

In a similar manner to Example 2, the suppressive effects of Peptides (I), (VII) to (XIV) on the anti-OVA antibody production in mice were measured. The results are shown in Table 6.

TABLE 6

| Treated with | Anti-OVA antibody titer |
|---|---|
| Peptide (I) | 23.8 ± 12.4 |
| Peptide (VII) | 20.9 ± 21.4 |
| Peptide (VIII) | 65.3 ± 34.7 |
| Peptide (IX) | 10.4 ± 6.3 |
| Peptide (X) | 49.8 ± 28.4 |
| Peptide (XI) | 15.3 ± 14.3 |
| Peptide (XII) | 50.9 ± 26.7 |
| Peptide (XIII) | 193.5 ± 155.9 |
| Peptide (XIV) | 90.9 ± 89.5 |
| Physiological saline (non-administered group) | 151.0 ± 25.3 |

The antibody production of the mice to which Peptide (VII), (IX) or (XI) had been administered was significantly suppressed compared with the non-administered group and Peptide (I) administered group. The antibody production of the mice to which Peptide (XIII) or (XIV) has been administered was, on the other hand, not suppressed compared with Peptide (I) administered group. Incidentally, each group consisted of 8 mice.

From Examples 7 and 8, it has been found that a peptide having suppressive effects on antigen nonspecific antibody production is required to have Ala, Leu and Phe at the first, third and fifth positions of its amino acid sequence, respectively, for the antibody production suppression.

We claim:

1. A peptide having the following amino acid sequence:
Ala-Xaa1-Leu-Xaa2-Phe-Xaa3-Xaa4-Xaa5-(Xaa6)n
wherein Xaa1 and Xaa4 each independently represents a naturally occurring amino acid residue which has an alkyl or heteroalkyl side chain which may be substituted by a hydroxy, amino or guanidyl group;
Xaa2 and Xaa6 each independently represents a naturally occurring amino acid residue which has an alkyl or heteroalkyl side chain which may be substituted by a hydroxyl group;
Xaa3 and Xaa5 each independently represents a naturally occurring amino acid residue which has a hydrophobic side chain; and
n stands for 1 or 0, with the proviso that the case where Xaa2 represents glycine is excluded,
or a derivative thereof.

2. A peptide or derivatives thereof according to claim 1, wherein n stands for 1 or 0;
Xaa1 and Xaa4 each independently represents any one of Lys, Arg, His and Ala;
Xaa2 and Xaa6 each independently represents Thr or Ala;
Xaa3 and Xaa5 each independently represents Gly or Ala.

3. A peptide or derivatives thereof according to claim 1, which has an amino acid sequence selected from the group consisting of the following amino acid sequences:
Ala-Lys-Leu-Thr-Phe-Gly-Lys-Gly-Thr,
Ala-Lys-Leu-Thr-Phe-Gly-Lys-Gly,
Ala-Ala-Leu-Thr-Phe-Gly-Lys-Gly,
Ala-Lys-Leu-Ala-Phe-Gly-Lys-Gly,
Ala-Lys-Leu-Thr-Phe-Ala-Lys-Gly,
Ala-Lys-Leu-Thr-Phe-Gly-Ala-Gly and
Ala-Lys-Leu-Thr-Phe-Gly-Lys-Ala.

4. A peptide or derivatives thereof according to claim 1, wherein the amino acid sequence is partially or entirely in the D-form.

5. A peptide or derivatives thereof according to claim 1, wherein the amino group at the N-terminal has been substituted with a protective group.

6. A peptide or derivatives thereof according to claim 5, wherein the protective group of the amino group at the N-terminal is an acetyl or t-butoxycarbonyl group.

7. A peptide or derivatives thereof according claim 1, wherein the carboxyl group at the C-terminal is a carboxy derivative.

8. A peptide or derivatives thereof according to claim 7, wherein the carboxy derivative at the C-terminal is an amide group.

9. A peptide or derivatives thereof according claim 1, which is a peptide selected from the group consisting of peptide represented by the following formulas (I) to (XII):

| | |
|---|---|
| Ala-Lys-Leu-Thr-Phe-Gly-Lys-Gly-Thr | (I) |
| DAla-DLys-DLeu-DThr-DPhe-Gly-DLys-Gly-DThr | (II) |
| Ac-Ala-Lys-Leu-Thr-Phe-Gly-Lys-Gly-Thr | (III) |
| tBoc-Ala-Lys-Leu-Thr-Phe-Gly-Lys-Gly-Thr | (IV) |
| Ac-DAla-DLys-DLeu-DThr-DPhe-Gly-DLys-Gly-DThr | (V) |
| Ac-DAla-DLys-DLeu-DThr-DPhe-Gly-DLys-Gly-DThr-NH2 | (VI) |
| Ala-Lys-Leu-Thr-Phe-Gly-Lys-Gly | (VII) |
| Ala-Ala-Leu-Thr-Phe-Gly-Lys-Gly | (VIII) |
| Ala-Lys-Leu-Ala-Phe-Gly-Lys-Gly | (IX) |
| Ala-Lys-Leu-Thr-Phe-Ala-Lys-Gly | (X) |
| Ala-Lys-Leu-Thr-Phe-Gly-Ala-Gly | (XI) and |
| Ala-Lys-Leu-Thr-Phe-Gly-Lys-Ala | (XII) |

(wherein D represents a D-form, Ac represents an acetyl group and tBoc represents a t-butoxycarbonyl group), or a derivative thereof.

10. A composition comprising at least one peptide or derivatives thereof as claimed in claim 1.

* * * * *

UNITED STATES PATENT AND TRADEMARK OFFICE
CERTIFICATE OF CORRECTION

PATENT NO.: 6,034,064
DATED: March 7, 2000
INVENTORS: Nobuyuki YAMAGATA et al.

It is certified that an error appears in the above-identified patent and that said Letters Patent is hereby corrected as shown below:

Claim 4, Column 21, line 48, after "according", insert --to--.

Claim 5, Column 21, line 51, after "according", insert --to--.

Claim 7, Column 22, line 15, after "according", insert --to--.

Claim 9, Column 22, line 21, after "according", insert --to--.

Signed and Sealed this

Thirteenth Day of March, 2001

*Attest:*

NICHOLAS P. GODICI

*Attesting Officer*   *Acting Director of the United States Patent and Trademark Office*